(12) United States Patent
Yoneta et al.

(10) Patent No.: US 11,925,935 B2
(45) Date of Patent: Mar. 12, 2024

(54) PARTICLE SEPARATION DEVICE AND PARTICLE SEPARATION APPARATUS

(71) Applicant: KYOCERA Corporation, Kyoto (JP)

(72) Inventors: Masashi Yoneta, Kagoshima (JP); Jumpei Nakazono, Kirishima (JP); Yuji Masuda, Yasu (JP)

(73) Assignee: KYOCERA CORPORATION, Kyoto (JP)

( * ) Notice: Subject to any disclaimer, the term of this patent is extended or adjusted under 35 U.S.C. 154(b) by 640 days.

(21) Appl. No.: 17/269,562

(22) PCT Filed: Aug. 27, 2019

(86) PCT No.: PCT/JP2019/033524
§ 371 (c)(1),
(2) Date: Feb. 19, 2021

(87) PCT Pub. No.: WO2020/045434
PCT Pub. Date: Mar. 5, 2020

(65) Prior Publication Data
US 2021/0322985 A1 Oct. 21, 2021

(30) Foreign Application Priority Data
Aug. 28, 2018 (JP) .................. 2018-159201

(51) Int. Cl.
*G01N 33/68* (2006.01)
*A01N 1/02* (2006.01)
(Continued)

(52) U.S. Cl.
CPC . *B01L 3/502761* (2013.01); *B01L 2200/0647* (2013.01); *B01L 2300/0816* (2013.01); *G01N 33/56972* (2013.01)

(58) Field of Classification Search
CPC ....... B01L 3/502761; B01L 2200/0647; B01L 2300/0816; B01L 2200/0652; B01L 2300/0627; B01L 2300/0681; B01L 2300/0864; B01L 2300/0887; B01L 2400/086; C12M 47/04; G01N 33/56972;
(Continued)

(56) References Cited

U.S. PATENT DOCUMENTS

2007/0102362 A1* 5/2007 Iida ................... B01L 3/502753
210/656

FOREIGN PATENT DOCUMENTS

JP      2012-076016 A    4/2012

\* cited by examiner

*Primary Examiner* — Jennifer Wecker
*Assistant Examiner* — Oyeleye Alexander Alabi
(74) *Attorney, Agent, or Firm* — Volpe Koenig

(57) ABSTRACT

A particle separation device comprises, inside a plate-like base body, a straight main flow path including a flow inlet and a plurality of branch flow paths. The flow inlet includes a sample flow inlet and a pressing flow inlet. The sample flow inlet is connected to the main flow path via a first bending part, a first straight part, a second bending part, and a second straight part. Widths in the first bending part and the first straight part are larger than widths in the second bending part and the second straight part. The widths in the second bending part and the second straight part are larger than a width in the main flow path. The pressing flow inlet is connected to the side surface of the main flow path via a third straight part, a third bending part, a fourth straight part, and a fifth straight part.

8 Claims, 14 Drawing Sheets

(51) Int. Cl.
*B01L 3/00* (2006.01)
*C07C 309/65* (2006.01)
*C07C 309/73* (2006.01)
*G01N 1/40* (2006.01)
*G01N 21/01* (2006.01)
*G01N 21/31* (2006.01)
*G01N 21/33* (2006.01)
*G01N 21/64* (2006.01)
*G01N 27/414* (2006.01)
*G01N 33/52* (2006.01)
*G01N 33/532* (2006.01)
*G01N 33/543* (2006.01)
*G01N 33/569* (2006.01)
*G01N 33/72* (2006.01)
*G01N 35/04* (2006.01)

(58) Field of Classification Search
CPC ....... G01N 15/1459; G01N 2015/0065; G01N 2015/149
See application file for complete search history.

PARTICLE SEPARATION DEVICE AND PARTICLE SEPARATION APPARATUS

CROSS-REFERENCE TO RELATED APPLICATION

The present application is a National Phase entry based on PCT Application No. PCT/JP2019/033524 filed on Aug. 27, 2019, entitled "PARTICLE SEPARATION DEVICE AND PARTICLE SEPARATION APPARATUS", which claims the benefit of Japanese Patent Application No. 2018-159201, filed on Aug. 28, 2018, entitled "PARTICLE SEPARATION DEVICE AND PARTICLE SEPARATION APPARATUS". The contents of which are incorporated by reference herein in their entirety.

FIELD

Embodiments of the present disclosure relate generally to a particle separation device and a particle separation apparatus used for separating specific particles from plural types of particles contained in a liquid.

BACKGROUND

Conventionally known is a particle separation device including a flow inlet and a plurality of flow outlets to separate and extract particles in a liquid using a minute flow path structure with a width of several μm to several hundred μm (micro flow path). In such a particle separation device, for example, when a liquid (for example, blood) containing plural types of particles (for example, erythrocyte and leukocyte) is flowed from the flow inlet, desired particles (for example, leukocyte) therein can be separated, and the desired particles and the other particles can be separately extracted from the plurality of flow outlets.

Subsequently, a type, the number, a concentration, or an optical property, for example, of the desired particles which have been separated and extracted is measured.

SUMMARY

A particle separation device and a particle separation apparatus are disclosed. In one embodiment, a particle separation device comprises: inside a plate-like base body, a straight main flow path including a flow inlet and a flow outlet opened in at least one of an upper surface and a lower surface of the base body and a plurality of branch flow paths connected to a portion midway through a side surface of the main flow path in a direction perpendicular to the side surface, wherein the flow inlet includes a sample flow inlet through which a sample which is a fluid containing particles to be separated flows toward the main flow path and a pressing flow inlet connected to a side surface of the main flow path located on an upstream side and opposite to the plurality of branch flow paths in a direction perpendicular to the side surface of the main flow path so that a fluid generating a pressing flow flows through the pressing flow inlet, in a planar view of the base body, the sample flow inlet is connected to the main flow path via an R-shaped first bending part, a first straight part, an R-shaped second bending part, and a second straight part, a width in the first bending part and a width in the first straight part are larger than a width in the second bending part and a width in the second straight part, and the width in the second bending part and the width of the second straight part are larger than a width in the main flow path, the pressing flow inlet is connected to the side surface of the main flow path via a third straight part, an R-shaped third bending part, a fourth straight part, and a fifth straight part, and a width in the third straight part is larger than a width in the fourth straight part, and the width in the fourth straight part is larger than a width in the fifth straight part.

In one embodiment, a particle separation apparatus comprises the particle separation device described above, a first pump for flowing the sample into the sample flow inlet and a second pump for flowing a fluid into the pressing flow inlet.

DETAILED DESCRIPTION

Used for separating desired particles in a liquid using a micro flow path is a particle separation device having a configuration of using a micro flow path in which a plurality of branch flow paths are connected to a main flow path and flowing a sample which is a liquid containing plural types of particles with particles to be separated and a fluid generating a pressing flow from the main flow path to the plurality of branch flow paths into the particle separation device respectively. It is desirable to flow the sample without a retention and unevenness of the particles when the sample is flowed in the micro flow path for the separation. Desired accordingly is a particle separation device having an advantageous configuration for efficiently separating desired particles in a lead-in part for the sample and the fluid.

Examples of a particle separation device according to the present disclosure, a measurement flow path device including the particle separation device, a particle separation apparatus, and a measurement apparatus are described hereinafter with reference to the drawings. In the present disclosure, a rectangular coordinate system (X, Y, Z) is defined for descriptive purposes to define a positive side in a Z axis direction as an upper side, however, in the present disclosure, any direction may be the upper side or a lower side. The following contents exemplifies embodiments of the present disclosure, and the present disclosure is not limited to these embodiments.

(Measurement Flow Path Device 1)

Figure 1:
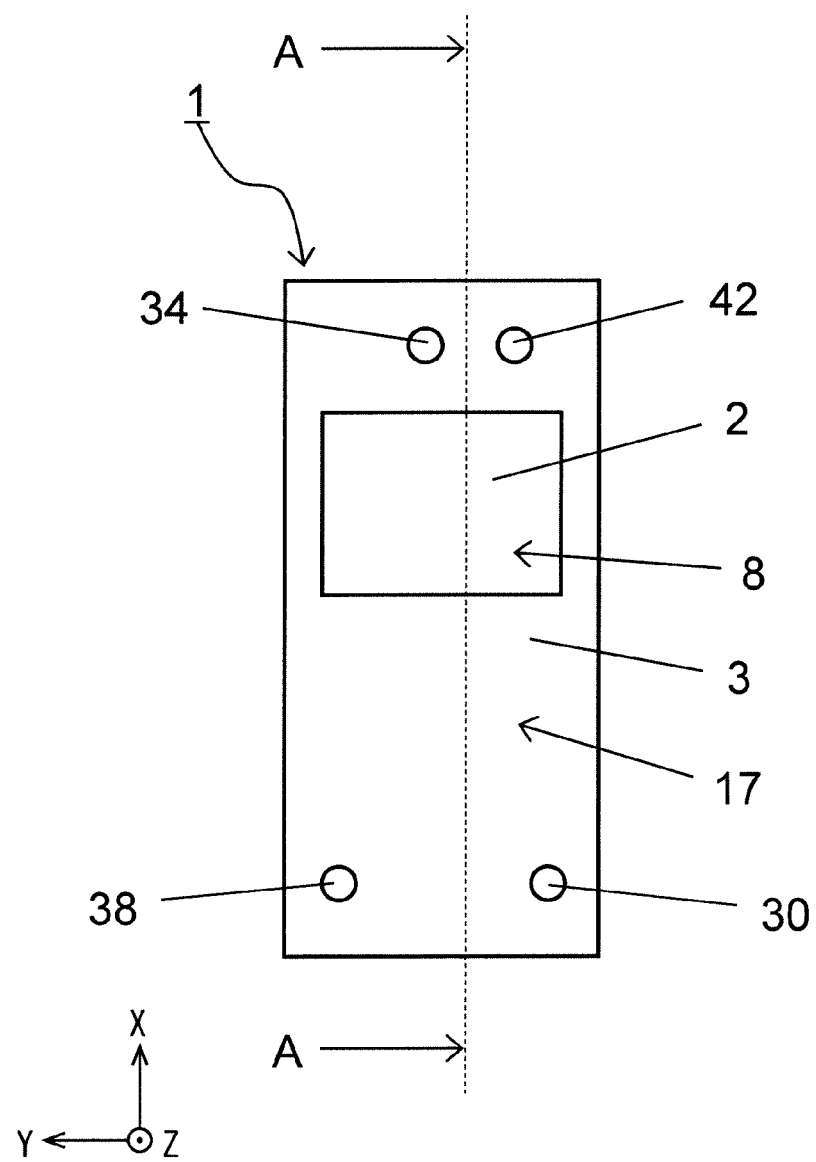
FIG. 1 illustrates a top view showing an example of a measurement flow path device including a particle separation device according to the present disclosure.
Figure 2:
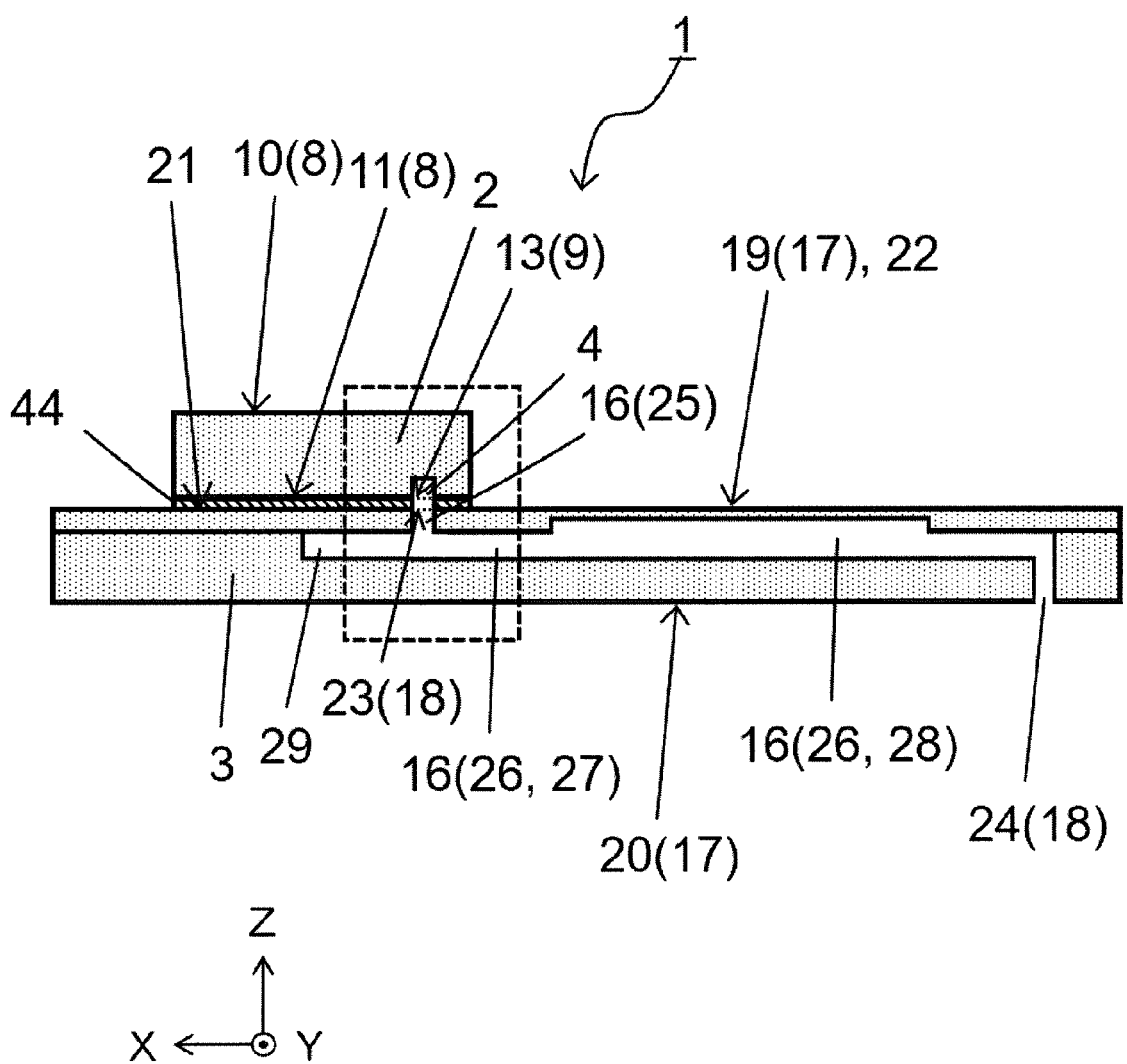
FIG. 2 illustrates a cross-sectional view showing an example of the measurement flow path device including the particle separation device according to the present disclosure.

FIG. 1 and FIG. 2 schematically illustrate an example of a measurement flow path device including a particle separation device according to the present disclosure. FIG. 1 is a top view of a measurement flow path device 1, and FIG. 2 is a cross-sectional view of the measurement flow path device 1 cut along an A-A line in FIG. 1.

When a fluid (a sample) containing particles to be measured is flowed in the measurement flow path device 1, the measurement flow path device 1 can separate and recover particles to be separated, which is a specific component in the sample, so that the specific component (separated particles) can be measured. For example, the measurement flow path device 1 can separate and recover white blood cells (leukocyte) which are specific components from blood, so that the number of white blood cells can be measured. The measurement flow path device 1 includes a first flow path device 2 which is a particle separation device and a second flow path device 3 connected to the first flow path device 2.

Figure 3:
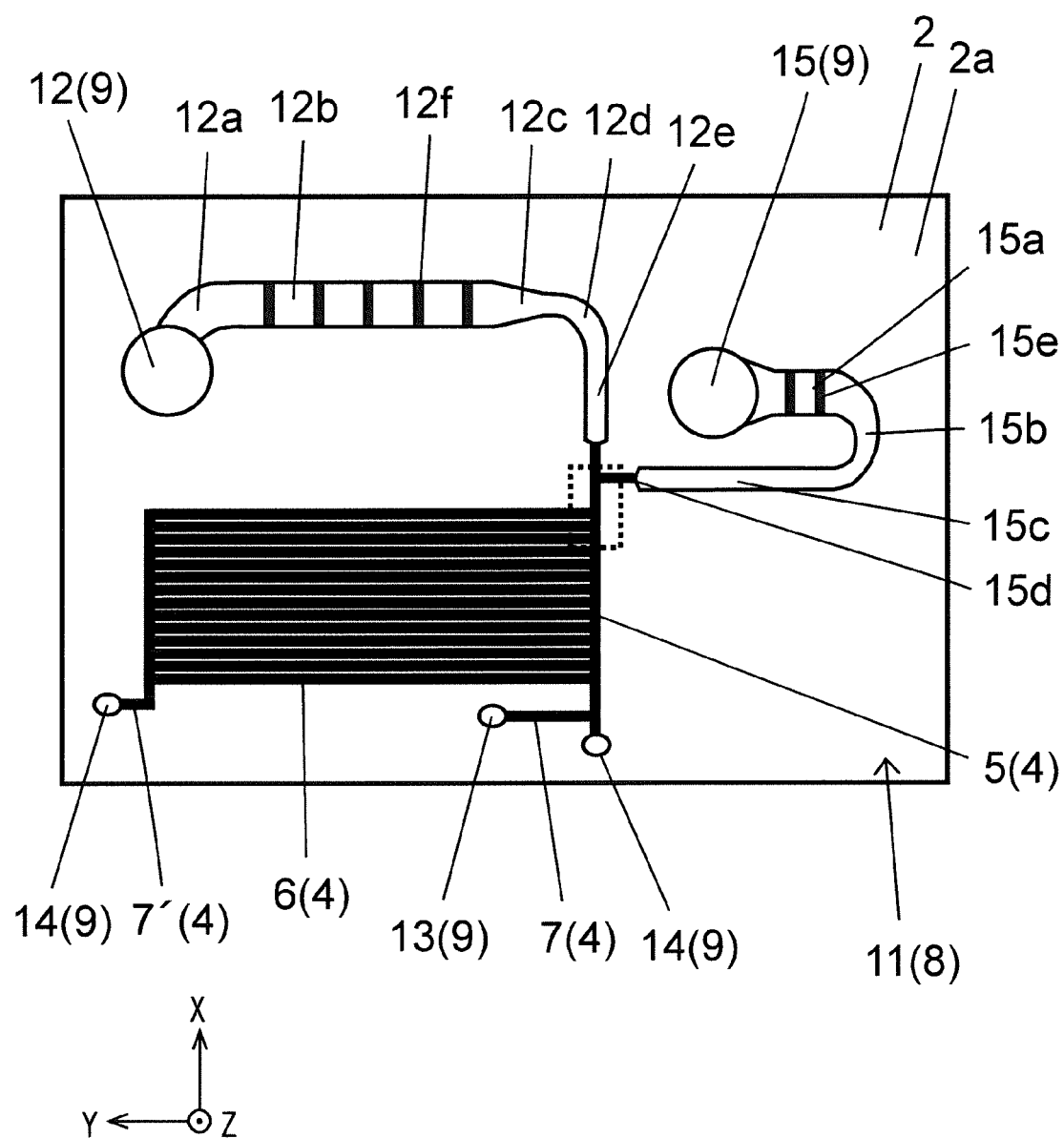
FIG. 3 illustrates a plan view showing an example of the particle separation device according to the present disclosure.

FIG. 3 schematically illustrates an example of the first flow path device 2 which is the particle separation device. FIG. 3 is a plan view of the first flow path device 2 when seen from an upper surface transparently.

(Particle Separation Device: First Flow Path Device 2)

The first flow path device 2 is the particle separation device capable of separating and recovering particles to be separated from a liquid (sample) containing plural types of particles. The first flow path device 2 includes a first flow path 4 inside a plate-like base body 2a. The first flow path 4 includes a linear main flow path 5 and a plurality of branch flow paths 6 branching from the main flow path 5. In the first flow path device 2 in the present disclosure, the sample (for example, blood) flowing in the first flow path device 2 flows into the main flow path 5, and particles (second particles, for example, red blood cells) different from specific particles (first particles, for example, white blood cells) flow from the main flow path 5 into the branch flow path 6, thus the specific particles (first particles) in the sample can be separated. When the second particles flow into the branch flow path 6, second particles can be separated from the sample.

The branch flow path 6 is designed so that the second particles flow therein by the branch, however, only the second particles do not necessarily flow therein. That is to say, particles different from the second particles (third particles, for example) may flow into the branch flow path 6 in some cases.

Figure 4:
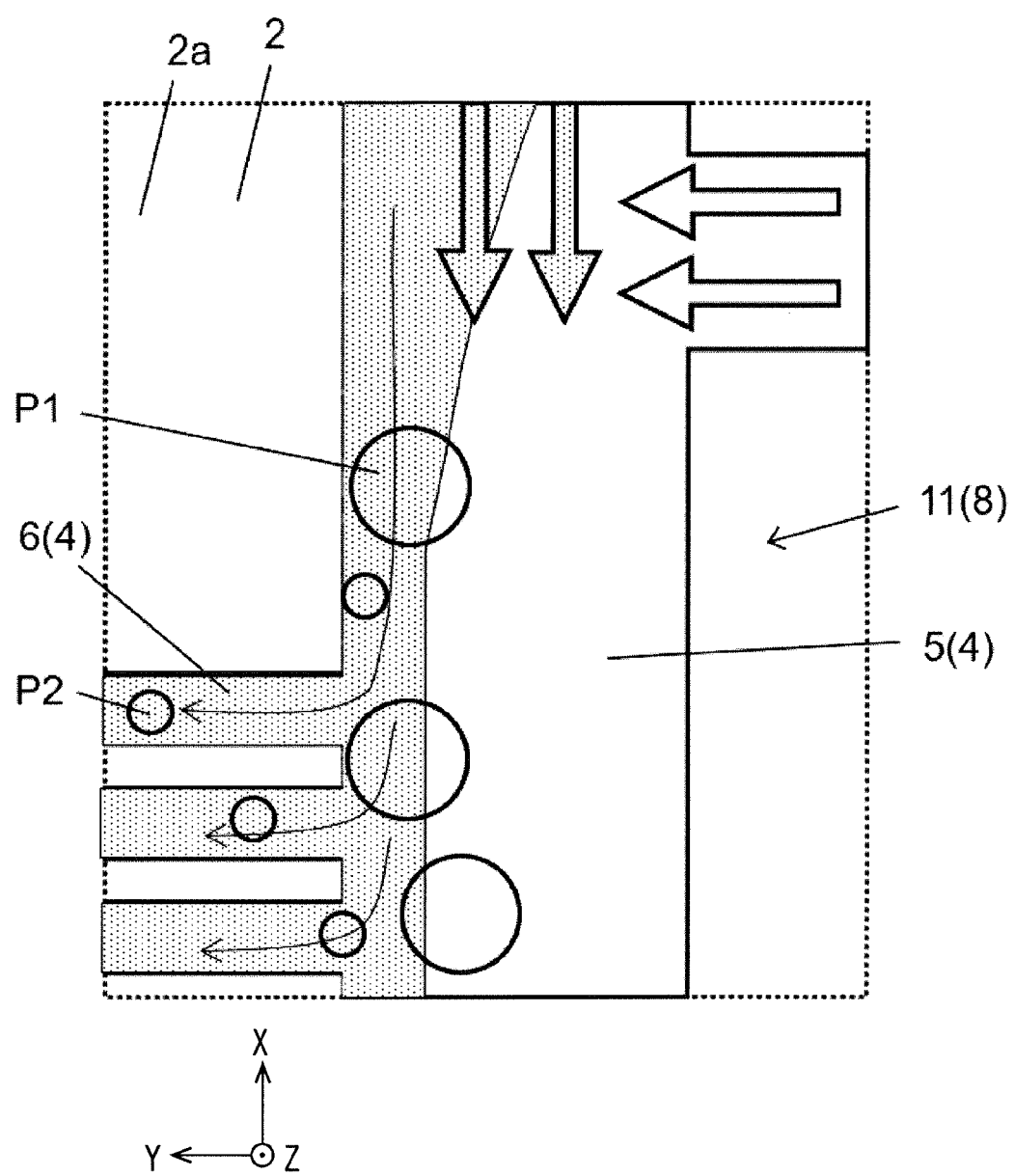
FIG. 4 illustrates a plan view showing a part of an example of the particle separation device according to the present disclosure.

FIG. 4 schematically illustrates a process of separating the first particles and the second particles. FIG. 4 is a plan view of enlarging a broken line section illustrated in FIG. 3. In FIG. 4, a large circle indicates a first particle P1 and a small circle indicates a second particle P2. A hatched arrow along an X axis direction indicates a main stream and a white outline arrow along a Y axis direction indicates a "pressing flow" described hereinafter. A hatched region in FIG. 4 indicates a "lead-in flow" described hereinafter.

The first flow path 4 in the present disclosure includes one main flow path 5 and the plurality of branch flow paths 6 connected to a portion midway through a side surface of one main flow path 5 in a direction perpendicular to the side surface thereof. In the first flow path device 2, a sectional area and length of each of the main flow path 5 and the branch flow path 6 and a flow rate of the sample are adjusted, thus the "lead-in flow", which flows from the main flow path 5 into the branch flow path 6 can be generated in the main flow path 5. The first flow path device 2 generates the pressing flow, which can press the sample flowing in the main flow path 5 against a side of the branch flow path 6, in the first flow path 4. As a result, as illustrated in FIG. 4, a width of the branch flow path 6 into which the lead-in flow flows is set to smaller than a size of the first particle P1 as the specific particle flowing in the sample and larger than a size of the second particle P2 as the other particle, thus the second particles P2 can be lead in the branch flow path 6. A width of the lead-in flow pressed by the pressing flow and flowing on the side of the branch flow path 6 in the main flow path 5 is set to larger than a barycentric position of the second particle P2 flowing in the sample and smaller than a barycentric position of the first particle P1, thus the second particles P2 can be effectively lead in the branch flow path 6. Accordingly, the first particles P1 which are the specific particles in the sample can be separated and recovered by being placed on a stream of the main flow path 5. At the same time, the second particles P2 can be separated from the sample and recovered by being placed on a stream of the branch flow path 6.

Particularly, the first flow path device 2 according to the present disclosure can be preferably used for separating red blood cells and white blood cells in blood as the sample. Herein, a size of the red blood cell in the blood is 7 to 8 μm, for example, and a barycentric position of the red blood cell is located 2 to 2.5 μm from an edge thereof, for example. A size of the white blood cell is 6 to 30 μm, for example, and a barycentric position of the white blood cell is located 5 to 10 μm from an edge thereof, for example. In this case, the main flow path 5 may have a sectional area ranging from 300 $\mu m^2$ to 1000 $\mu m^2$ and a length ranging from 0.5 mm to 20 mm, for example. A dimension of the cross section may have a width of approximately 30 μm and a height of approximately 20 μm within a range of the sectional area described above, for example. The branch flow path 6 may have a sectional area ranging from 100 $\mu m^2$ to 500 $\mu m^2$ and a length ranging from 3 mm to 25 mm, for example. A dimension of the cross section may have a width of approximately 15 μm and a height of approximately 20 μm within a range of the sectional area described above, for example. The flow rate in the first flow path 4 may be equal to or larger than 0.2 m/s and equal to or smaller than 5 m/s, for example. As a result, the width of the lead-in flow can be set equal to or larger than 2 µm and equal to or smaller than 10 µm, for example, thus the red blood cell and the white blood cell can be effectively separated from the blood.

The first flow path device 2 includes a plurality of first openings 9 opened in at least one of an upper surface and a lower surface of the base body 2a. At least two of the first openings 9 are flow inlets for flowing the sample into the main flow path 5. The flow inlet includes a sample flow inlet 12 through which a sample which is a fluid containing particles (for example, the first particles P1) to be separated flows toward the main flow path 5 and a pressing flow inlet 15 connected to the side surface of the main flow path 5 located on an upstream side and opposite to the plurality of branch flow paths 6 in a direction perpendicular to the side surface of the main flow path 5 so that a fluid generating the pressing flow flows through the pressing flow inlet 15.

In the first flow path device 2 of the present disclosure, the sample flow inlet 12 is connected to the main flow path 5 via an R-shaped first bending part 12a, a first straight part 12b leading from the first bending part 12a, an R-shaped second bending part 12d, and a second straight part 12e leading from the second bending part 12d. With regard to a width of the flow path from the sample flow inlet 12 to the main flow path 5, a width in the first bending part 12a and a width in the first straight part 12b are larger than a width in the second bending part 12d and a width in the second straight part 12e, and the width in the second bending part 12d and the width of the second straight part 12e are larger than the width in the main flow path 5.

In this case, the first opening 9 as the sample flow inlet 12 may have a circular shape with a size of 1 to 3 mm, for example. The width in the first bending part 12a and the first straight part 12b may be set to 0.5 to 1.5 mm, for example. The width in the second bending part 12d and the second straight part 12e may be set to 0.3 to 0.5 mm, for example. A difference between the width in the first bending part 12a and the first straight part 12b and the width in the second bending part 12d and the second straight part 12e may be set to 0.2 to 1.2 mm, for example. The heights of these flow paths may be set to the same height as the first flow path 4. A depth of the sample flow inlet 12 may be a depth from the opening in the upper surface of the base body 2a to a bottom surface of the first bending part 12a, for example.

A large volume of particles flow in the vicinity of the sample flow inlet 12, thus it is important to reduce the retention of the particles. The flow rate is low in the vicinity of the inlet, thus there is a possibility that a part where the particles hardly flow occurs if the flow path is sharply bent. In consideration of the above condition, a size of R (curvature radius) of the R-shaped first bending part 12a may be 1 mm or more, for example. A range of the first bending part 12a (intersection angle: corresponding to a center angle of an arc from an entrance to an exit of the bending part with respect to a center of the curvature radius) may be approximately 90° or less, for example, by reason that the particles hardy remain when a flexion angle is small. The second bending part 12d has the width narrower than the first bending part 12a, thus a flow rate in the second bending part 12d is higher. Accordingly, a size of R (curvature radius) of the R-shaped second bending part 12d may be approximately 1 mm or more, for example, as with the first bending part 12a to flow the sample smoothly. A range (intersection angle) of the second bending part 12d may be approximately 90° or less, for example, by reason that the particles hardy remain when a flexion angle is small.

The sample flow inlet 12 is connected to the main flow path 5 via the flow path having such a configuration, thus the R-shaped first bending part 12a and second bending part 12d allow the sample to pass therethrough smoothly and can reduce the retention of the particles. The first straight part 12b and the second straight part 12e can ensure linearity in the flow of the sample, and can flow the sample into the main flow path 5 while reducing the unevenness of the particles.

The pressing flow inlet 15 is connected to the side surface of the main flow path 5 via a third straight part 15a, a third bending part 15b leading from the third straight part 15a, a fourth straight part 15c leading from the third bending part 15b, and a fifth straight part 15d leading from the fourth straight part 15c. With regard to a width of the flow path from the pressing flow inlet 15 to the main flow path 5, a width in the third straight part 15a is larger than a width in the fourth straight part 15c, and the width in the fourth straight part 15c is larger than a width in the fifth straight part 15d.

In this case, the first opening 9 as the pressing flow inlet 15 may have a circular shape with a size of 1 to 3 mm, for example. The width in the third straight part 15a may be set to 0.5 to 1.5 mm, for example. The width in the fourth straight part 15c may be set to 0.3 to 0.5 mm, for example. The width in the fifth straight part 15d may be set to 0.03 to 0.05 mm (30 to 50 µm), for example. A difference between the width in the third straight part 15a and the width in the fourth straight part 15c may be set to 0.2 to 1.2 mm, for example. A difference between the width in the fourth straight part 15c and the width in the fifth straight part 15d may be set to 0.27 to 0.47 mm (270 to 470 µm), for example. The heights of these flow paths may be set to the same height as the first flow path 4. A depth of the pressing flow inlet 15 may be a depth from the opening in the upper surface of the base body 2a to a bottom surface of the third straight part 15a, for example.

A size of R (curvature radius) of the R-shaped third bending part 15b is not particularly limited by reason that the fluid for the pressing flow does not contain the particles, thus may be appropriately set in consideration of downsizing of the flow path. A range (intersection angle) of the third bending part 15b is not particularly limited by reason that the fluid does not contain the particles, thus may be appropriately set to approximately 180° or less, for example, in consideration of downsizing of the flow path as with the size of R.

The pressing flow inlet 15 is connected to the side surface of the main flow path 5 via the flow path having such a configuration, thus the R-shaped third bending part 15b allows downsizing of a lead-in part for the fluid generating the pressing flow, and allows the fluid to pass therethrough smoothly. The fourth straight part 15c and the fifth straight part 15d can ensure linearity in the flow of the fluid, and can flow the fluid in which unevenness of the flow is suppressed into the main flow path 5 as a preferable pressing flow. The pressing flow inlet 15 is connected to the side surface of the main flow path 5 via the flow path from the fourth straight part 15c having the large width to the fifth straight part 15d having the small width, thus this can provide the fluid with a pressure and a flow rate appropriate for the fluid flowing into the main flow path 5 to generate the pressing flow, and can flow the fluid having a favorable linearity. Accordingly, the main flow path 5 and the branch flow path 6 can effectively separate the particles.

In the leading-part for the sample, the first straight part 12b and the second bending part 12d are preferably connected by a tapered part 12c in which a width is gradually narrowed. According to such a configuration, the particles in the sample can be collected smoothly and flowed into the main flow path 5. A length of the tapered part 12c may be appropriately set in accordance with the difference between the width in the first straight part 12b and the width in the second bending part 12d in consideration of collecting the particles to a center of the flow while reducing a rapid pressure change, thus may be set to 0.5 to 2 mm, for example.

In the lead-in part for the fluid for the pressing flow, the third bending part 15b preferably has the width gradually narrowed from the third straight part 15a to the fourth straight part 15c. The downsizing of the flow path of the fluid is achieved and the width of the flow path in the third bending part 15b is narrowed, thus the fluid can be provided with the pressure appropriate for flowing into the main flow path 5 as the pressing flow via the subsequent fourth straight part 15c and fifth straight part 15d. Such a configuration is preferable in effectively separating the particles by the main flow path 5 and the branch flow path 6.

In the lead-in part for the sample, it is preferable that the first straight part 12b is provided with a pillar part 12f made up of a plurality of pillar bodies, which are disposed in a width direction of the flow path, each extending from a bottom surface to a ceiling surface of the flow path. According to such a configuration, if a foreign material such as a dust, for example, is mixed into the sample in addition to the particles, the pillar part 12f can filter and remove the foreign material, thus an influence of the foreign material on the separation of the particles to be separated can be eliminated. Applicable as a size and a shape of each pillar body constituting such a pillar part 12f is a columnar shape with a diameter of approximately 20 μm, a quadrangular prism shape with a side length of approximately 20 μm, or a quadrangular prism shape with a length of approximately 20 μm in a width direction and a length of approximately 60 μm in a flow direction. Applicable as the arrangement and the number of the pillar bodies is that the pillar bodies are arranged at intervals of approximately 30 μm in the width direction of the flow path and arranged in approximately three rows at intervals of approximately 30 μm in the flow direction. In the example illustrated in FIG. 3, the pillar parts 12f are located in five positions in the first straight part 12b, and when the plurality of pillar parts 12f are located, an interval between the pillar parts 12f may be set to approximately 0.5 to 1 mm, for example. The interval and the number of the pillar bodies may be changed between the plurality of pillar parts 12f. For example, when the particles are blood cells and the foreign material is relatively soft and has high viscosity, such as a blood clot, a risk of closure of the flow path due to a clogging caused by joining of the foreign materials can be reduced by setting the interval of the pillar bodies to be larger.

In the lead-in part for the fluid for the pressing flow, it is preferable that the third straight part 15a is provided with a pillar part 15e made up of a plurality of pillar bodies, which are disposed in a width direction of the flow path, each extending from a bottom surface to a ceiling surface of the flow path. According to such a configuration, if a foreign material such as a dust, for example, is mixed into the fluid, the pillar part 15e can filter and remove the foreign material, thus an influence of the foreign material on the fluid for the pressing flow can be eliminated in the manner similar to the pillar part 12f. A size, a shape, and an arrangement of the pillar bodies constituting such a pillar part 15e may be set in the manner similar to the pillar part 12f in accordance with a foreign material to be removed.

A length of the second straight part 12e in the lead-in part for the sample is preferably at least three times larger than the width of the second straight part 12e. A length of the fourth straight part 15c in the lead-in part for the fluid for the pressing flow is preferably at least three times larger than the width of the fourth straight part 15c. The length of the straight part is at least three times larger than the width of the straight part, thus linearity of the flow of the fluid in the flow path can be favorably ensured. Such a configuration can effectively reduce the influence of unevenness of the flow of the fluid caused by centrifugal force by the second bending part 12d located on the upstream side of the second straight part 12e and the third bending part 15b located on the upstream side of the fourth straight part 15c.

In the lead-in part for the fluid for the pressing flow, the fifth straight part 15d is set subsequent to the fourth straight part 15c, and the fifth straight part 15d is connected to the side surface of the main flow path 5. It is preferable that a length of the fifth straight part 15d is also at least three times larger than a width of the fifth straight part 15d. Accordingly, the linearity of the fluid ensured by the fourth straight part 15c can also be maintained by the fifth straight part 15d.

The first flow path 4 further includes a recovery flow path 7 connected to the main flow path 5, and can recover the first particles P1 using the recovery flow path 7. In the present disclosure, the first flow path 4 can recover the first particles P1 in the first recovery flow path 7 using the pressing flow.

The first flow path 4 may include a disposal flow path 7' connected to the plurality of branch flow paths 6. The disposal flow path 7' may recover or dispose of the second particles P2 separated in the branch flow paths 6. When the second particles P2 are recovered by the plurality of branch flow paths 6, one disposal flow path 7' to which the plurality of branch flow paths 6 are connected functions as a flow path for recovering the second particles P2. The fluid containing the first particles P1 and flowing from the main flow path 5 to the recovery flow path 7 may be disposed of in this case.

The first flow path device 2 is a member made up of the plate-like base body 2a. The first flow path 4 is located inside the plate-like base body 2a. The first flow path device 2 includes a pair of first upper and lower surfaces 8 located on top and bottom thereof in a thickness direction (the Z axis direction). The first flow path 4 includes the plurality of first openings 9 located and opened in at least one of the pair of first upper and lower surfaces 8.

In the present disclosure, one of the pair of first upper and lower surfaces 8 is defined as a first upper surface 10 and the other one thereof is defined as a first lower surface 11 for descriptive purposes. In the pair of first upper and lower surfaces 8, the first upper surface 10 is a surface located on a positive side of the Z axis and the first lower surface 11 is a surface located on a negative side of the Z axis. In the present disclosure, at least one of the plurality of first openings 9 is located in the first lower surface 11.

The plurality of first openings 9 include the sample flow inlet 12 through which the sample flows into the main flow path 5, a sample flow outlet 13 recovering the first particles P1 from the recovery flow path 7, and at least one disposal flow outlet 14 recovering a component in which the first particles P1 are removed from the sample. In the present disclosure, the plurality of first openings 9 include the pressing flow inlet 15 through which the fluid for the pressing flow for pressing the sample against the branch flow path 6 flows. In the present disclosure, the disposal flow outlet 14 is connected to the main flow path 5 and the disposal flow path 7'. The fluid flowing out through the disposal flow outlet 14 is recovered through a through hole 14' formed in the second flow path device 3.

A planar shape of the first flow path device 2 in the present disclosure is a rectangular shape. Each of the first upper and lower surfaces 8 is a flat surface. A planar shape of the first flow path device 2 is not limited to the rectangular shape. Each of the first upper and lower surfaces 8 is not limited to the flat surface. In the first upper and lower surfaces 8, shapes of the first upper surface 10 and the first lower surface 11 may be different from each other.

The first flow path device 2 may be formed of a material of polydimethylsiloxane (PDMS) or polymethylmethacrylate resin:acrylic (PMMA), for example. A thickness of the first flow path device 2 may be 1 to 5 mm, for example. When the planar shape of the first flow path device 2 is the rectangular shape, the first flow path device 2 may have a short side with a length of 10 to 30 mm and a long side with a length of 10 to 50 mm, for example. The first flow path device 2 can be manufactured by preparing two substrates, forming a groove, which is to be the first flow path 4, in one of the two substrates, and attaching the other substrate thereto to cover the groove, thereby forming the base body 2a including the first flow path 4 therein, for example.

(Second Flow Path Device 3)

The second flow path device 3 is a flow path device for measuring specific particles separated and recovered in the first flow path device 2, and constitutes a measurement flow path device with the first flow path device 2. As illustrated in FIG. 2, the second flow path device 3 includes a second flow path 16 connected to the first flow path 4 in the first flow path device 2. The second flow path device 3 has translucency. As a result, the second flow path device 3 can flow the specific particles separated and recovered in the first flow path device 2 to the second flow path 16 and measure the specific particles using an optical sensor described hereinafter. Specifically, the optical sensor measures intensity of light passing through the fluid containing the specific particles in the second flow path 16, thereby measuring the specific particles.

The second flow path device 3 is a member made up of the plate-like base body. The second flow path 16 is located inside the plate-like member. The second flow path device 3 includes a pair of second upper and lower surfaces 17 located on top and bottom thereof in a thickness direction (the Z axis direction). The second flow path 16 includes a plurality of second openings 18 located and opened in at least one of the pair of second upper and lower surfaces 17.

In the present disclosure, one of the pair of second upper and lower surfaces 17 is defined as a second upper surface 19 and the other one thereof is defined as a second lower surface 20 for descriptive purposes. In the pair of second upper and lower surfaces 17, the second upper surface 19 is a surface located on a positive side of the Z axis and the second lower surface 20 is a surface located on a negative side of the Z axis.

A planar shape of the second flow path device 3 in the present disclosure is a rectangular shape. Each of the second upper and lower surfaces 18 is a flat surface. A planar shape of the second flow path device 3 is not limited to the rectangular shape. Each of the second upper and lower surfaces 17 is not limited to the flat surface. In the second upper and lower surfaces 17, shapes of the second upper surface 19 and the second lower surface 20 may be different from each other.

The second flow path device 3 is formed of PMMA or cycloolefin polymer (COP), for example. A thickness of the second flow path device 3 may be 0.5 to 5 mm, for example. When the planar shape of the second flow path device 3 is the rectangular shape, the second flow path device 3 may have a short side with a length of 10 to 30 mm and a long side with a length of 20 to 50 mm, for example. The second flow path device 3 can be manufactured by preparing two substrates, forming a groove, which is to be the second flow path 16, in one of the two substrates, and attaching the other substrate thereto to cover the groove, thereby forming the base body including the second flow path 16 therein, for example.

Figure 5:
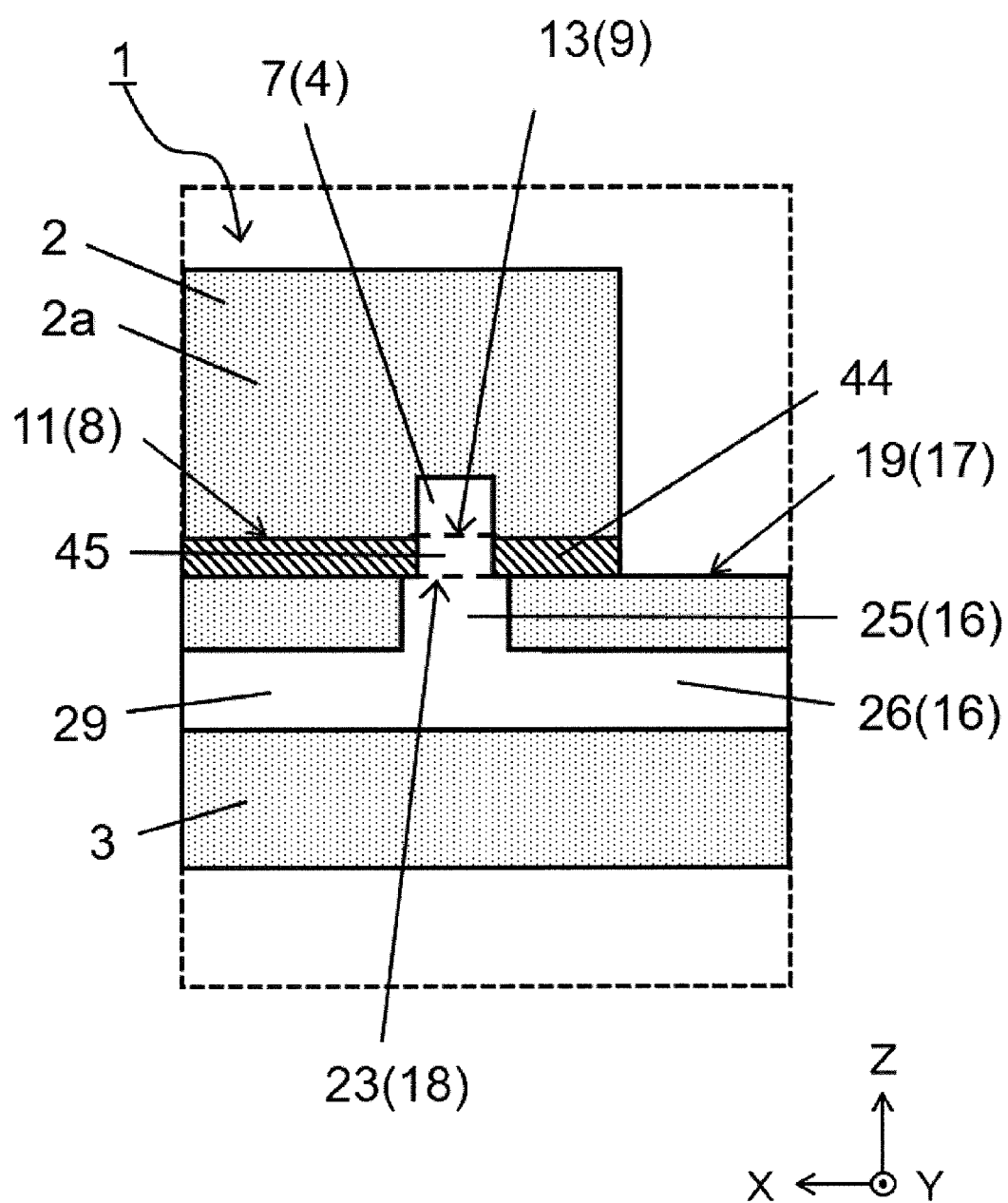
FIG. 5 illustrates a cross-sectional view showing a part of an example of the measurement flow path device including the particle separation device according to the present disclosure.

FIG. 5 schematically illustrates a part of an example of the measurement flow path device 1 including the first flow path device 2 which is the particle separation device and the second flow path device 3. FIG. 5 is a cross-sectional view of enlarging a broken line section illustrated in FIG. 2.

In the second flow path device 3 in the present disclosure, at least one of the plurality of second openings 18 is located in the second upper surface 19. The first flow path device 2 is located on the second upper surface 19 via the first lower surface 11, and the first opening 9 located in the first lower surface 11 and the second opening located in the second upper surface 19 are connected to each other. Accordingly, in the measurement flow path device 1 in the present disclosure, the first flow path device 2 is directly connected to the second flow path device 3, and the process from the separation and recovery to the measurement of the particles in the sample can be continuously performed, thus a work efficiency can be improved. The plate-like first flow path device 2 and second flow path device 3 are located to be stacked in the thickness direction, thus the measurement flow path device 1 can be minimized.

The second upper surface 19 of the second flow path device 3 in the present disclosure includes a first region 21 and a second region 22. In a plan view, the second flow path 16 in the second flow path device 3 is located to extend from the first region 21 to the second region 22, and the first flow path device 2 is located only in the first region 21 in the second flow path device 3. As a result, the second flow path 16 is located in the second region 22 not to overlap with the first flow path device 2, thus the second region 22 can be used as a measurement region for measuring the particles.

In the measurement flow path device 1, a member which can reflect light can be located in the second region 22 as described hereinafter.

The first flow path device 2 may be formed of a material different from that of the second flow path device 3. In the present disclosure, for example, the first flow path device 2 is formed of PDMS or the like, and the second flow path device 3 is formed of COP or the like.

As is the case in the present disclosure, the first flow path device 2 may be located on an upper side of the second flow path device 3. Specifically, the first flow path device 2 may be located on the second upper surface 19 of the second flow path device 3. As a result, the fluid containing the specific particles separated and recovered in the first flow path device 2 can be flowed into the second flow path device 3 also using gravity, and a retention of the fluid containing the specific particles midway through the flow path can be reduced.

The present disclosure does not exclude an embodiment in which the first flow path device 2 is located on the second lower surface 20 of the second flow path device 3.

The plurality of second openings 18 include a second sample flow inlet 23 through which the fluid containing the separated particles flows into the second flow path 16 and a second sample flow outlet 24 through which the fluid is recovered from the second flow path 16. The second sample flow inlet 23 has an opening located in the second upper surface 19, and is connected to the sample flow outlet 13 in the first flow path device 2. The second sample flow outlet 24 is located in the second lower surface 20. As a result, by using the gravity, the fluid can be easily flowed from the first flow path device 2 through the second sample flow inlet 23 and the fluid can be easily recovered in the second sample flow outlet 24.

The second opening 18 of the second sample flow outlet 24 is preferably larger than the first opening 9 of the sample flow outlet 13 as illustrated in FIG. 5. As a result, the retention of the fluid can be reduced in a connection part between the first flow path device 2 and the second flow path device 3. A size of the second sample flow outlet 24 may be 1 to 3 mm, for example. A size of the sample flow outlet 13 may be 1 to 3 mm, for example.

The second flow path 16 includes a vertical part 25 connected to the second sample flow inlet 23 (the second opening 18) and extending in the thickness direction and a planar part 26 connected to the vertical part 25 and extending along one direction of a planar surface. The second flow path 16 includes the vertical part 25, thereby being able to reduce the retention of the fluid in the connection part between the second flow path 16 and the first flow path 4. The second flow path 16 includes the planar part 26, thereby being able to retain the fluid in the planar part 26 in measuring the particles, thus a stable measurement can be achieved.

A width of the vertical part 25 may be 0.5 to 2 mm, for example, and a width of the planar part 26 may be 1 to 6 mm, for example. A length of the vertical part 25 may be 0.5 to 1 mm, for example, and a height of the planar part 26 may be 0.5 to 2 mm, for example.

Figure 6:
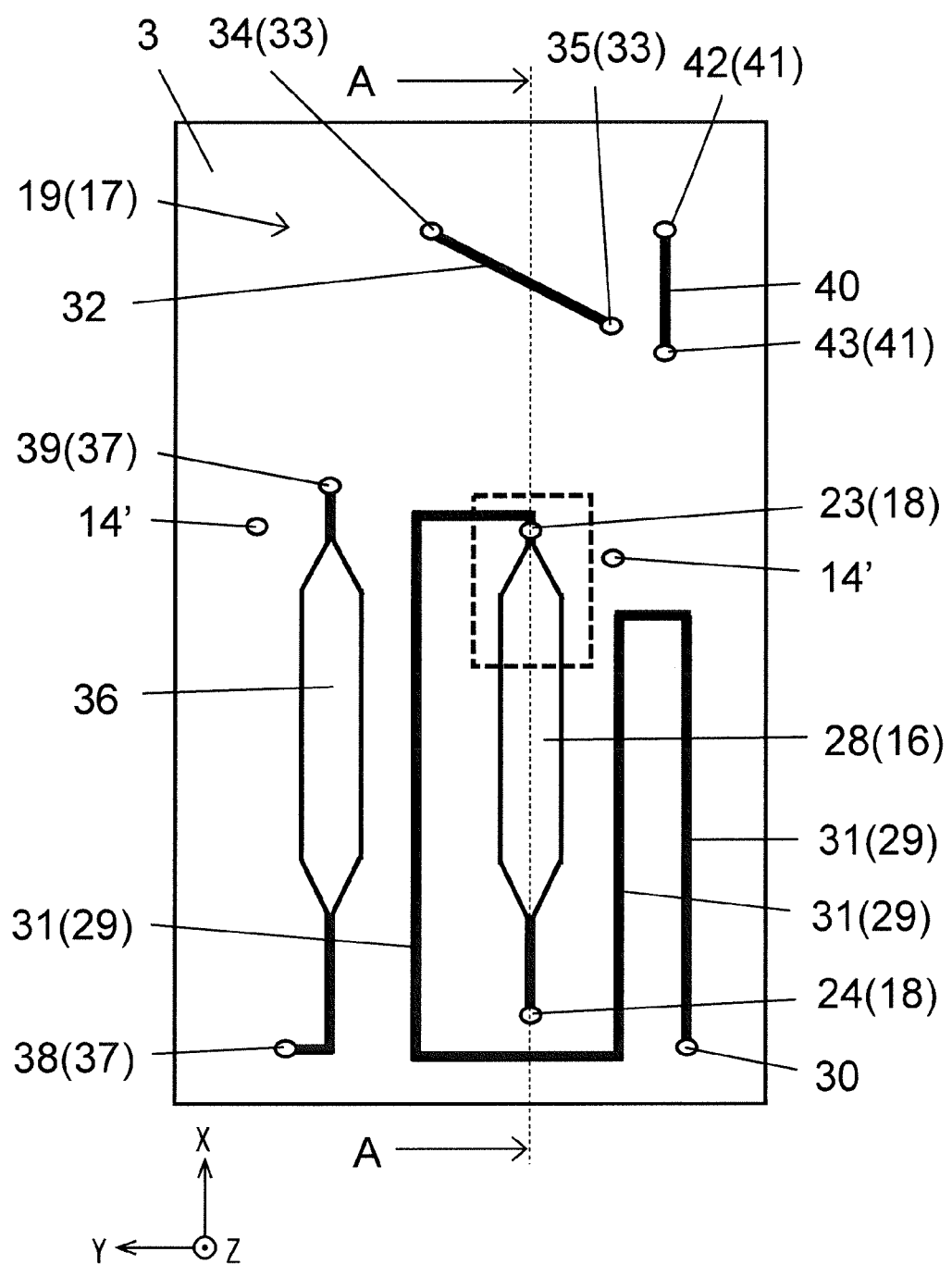
FIG. 6 illustrates a plan view showing an example of a second flow path device used for the measurement flow path device including the particle separation device according to the present disclosure.
Figure 7:
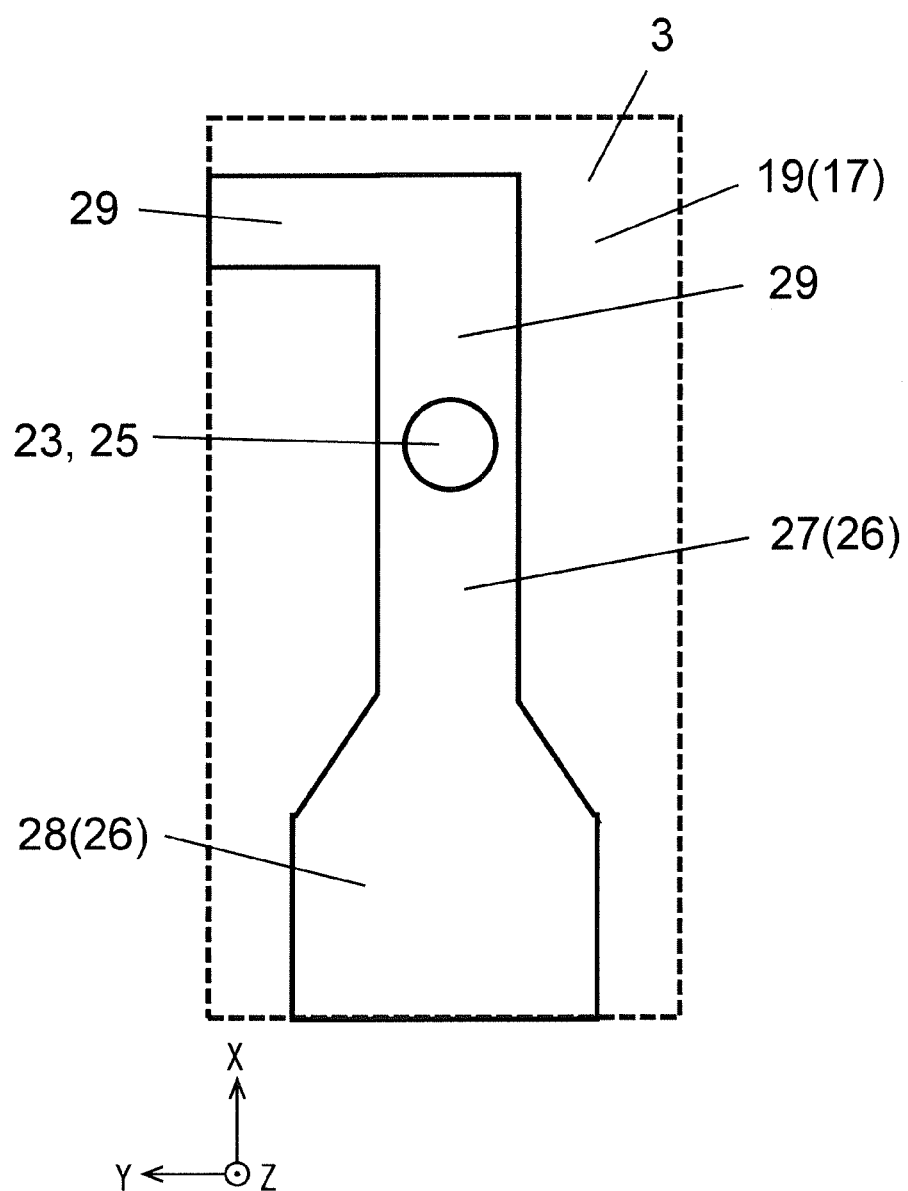
FIG. 7 illustrates a plan view showing a part of an example of the second flow path device used for the measurement flow path device including the particle separation device according to the present disclosure.

FIG. 6 and FIG. 7 schematically illustrate an example of the second flow path device 3 used in the measurement flow path device 1. FIG. 6 is a plan view of the second flow path device 3 when seen from an upper surface transparently. FIG. 7 is a plan view of enlarging a broken line section illustrated in FIG. 6. An A-A line in FIG. 6 indicates the same position as the A-A line in FIG. 1.

Part of the planar part 26 connected to at least the vertical part 25 preferably has a width larger than the vertical part 25. As a result, the retention of the fluid can be reduced in a connection part between the planar part 26 and the vertical part 25.

The planar part 26 may further include a first planar part 27 connected to the vertical part 25 and a second planar part 28 connected to the first planar part 27 and having a width larger than the first planar part 27. As a result, the first particles P1, for example, separated and recovered in the first flow path device 2 can be easily diffused in the second planar part 28. A width of the first planar part 27 may be 0.5 to 3 mm, for example. A width of the second planar part 28 may be 1 to 5 mm, for example. A width of the second planar part 28 may be twice or more and ten times or less than that of the first planar part 27, for example. In the present disclosure, a connection part between the first planar part 27 and the second planar part 28 is gradually widened.

The second planar part 28 preferably has a height larger than the first planar part 27. As a result, the first particles P1, for example, which are the separated specific particles can be easily diffused. A height of the first planar part 27 may be 0.2 to 1 mm, for example. A height of the second planar part 28 may be 1 to 5 mm, for example.

The second flow path device 3 may further include, in addition to the second flow path 16, a third flow path 29 connected to the second flow path 16. The third flow path 29 may be connected to the planar part 26 of the second flow path 16. The third flow path 29 has a function of sweeping away a fluid retaining in the planar part 26 by flowing gas or the like, for example. As a result, the retention of the fluid in the second flow path 16 can be reduced.

In the second flow path device 3 in the present disclosure, as illustrated in FIG. 5, FIG. 6, and FIG. 7, the third flow path 29 is located to be connected to the connection part between the vertical part 25 and the planar part 26 in the second flow path 16.

One end of the third flow path 29 is connected to the second flow path 16. The other end of the third flow path 29 serves as a third opening 30 located in the pair of second upper and lower surfaces 17. That is to say, the third flow path 29 includes the third opening 30 located in one of the pair of second upper and lower surfaces 17 (in the present disclosure, the second upper surface 19). The third opening 30 is an opening through which an extrusion fluid such as gas for sweeping away the fluid from the second planar part 28 of the second flow path 16 is flowed in.

At least part of the third flow path 29 connected to the second flow path 16 may extend along an extension direction of the planar part 26 (the first planar part 27) of the second flow path 16 as illustrated in FIG. 7.

At least part of the third flow path 29 connected to the second flow path 16 preferably has the same shape as at least part of the second flow path 16 connected to the third flow path 29. As a result, a difference in level does not occur between the second flow path 16 and the third flow path 29, and the retention of the fluid in the difference in level of the connection part can be reduced.

The third flow path 29 preferably includes a plurality of straight parts 31 each extending in predetermined one direction and arranged in a direction intersecting with the one direction. The third flow path 29 includes the plurality of straight parts 31, thereby being able to reduce the fluid flowing back from the second flow path 16 and leaked from the third opening 30.

The sample flow inlet 12 in the first openings 9 may be located in the same surface (the first lower surface 11 in the present disclosure) as that of the sample flow outlet 13 in the first openings 9. In this case, the sample flows into the first flow path device 2 from below (a negative side of the Z axis direction). As a result, the second particles P2 can be sunk when a specific gravity of the second particles P2 is larger than that of the first particles P1, thus the particles can be separated easily.

The second flow path device 3 may further include a fourth flow path 32 different from the second flow path 16 and the third flow path 29 as illustrated in FIG. 6. The fourth flow path 32 may include a plurality of fourth openings 33 located in at least one of the pair of second upper and lower surfaces 17. The fourth flow path 32 can function as a flow path in which the sample before the specific particles are separated flows. As a result, the sample is flowed into the fourth flow path 32 of the second flow path device 3 before flowed into the first flow path device 2, thus a foreign material which has been mixed into the sample to be flowed, for example, can be previously reduced.

The plurality of fourth openings 33 include a fourth flow inlet 34 and a fourth flow outlet 35. The fourth flow inlet 34 is an opening through which a sample flows into the fourth flow path 32. The fourth flow outlet 35 is an opening through which the sample flows from the fourth flow path 32. The fourth flow inlet 34 is opened to flow the sample into the flow path from outside, and the fourth flow outlet 35 is connected to the sample flow inlet 12 of the first flow path device 2.

The fourth flow inlet 34 and the fourth flow outlet 35 may be located in the second upper surface 19. In this case, an operation such as an external connection for flowing the sample into the flow path can be performed from above. In the present disclosure, the fourth flow inlet 34 is located in the same surface as that of the second sample flow outlet 24. In the present disclosure, the fourth flow outlet 35 is also located in the same surface as that of the second sample flow outlet 24. The fourth flow inlet 34 is located in the same surface as that of the third opening 30.

The second flow path device 3 may further include a fifth flow path 36 different from the second flow path 16, the third flow path 29, and the fourth flow path 32 as illustrated in FIG. 6. The second flow path 16 is a flow path flowing the specific particles separated and recovered in the first flow path device 2, and in contrast, the fifth flow path 36 is a flow path for correction. The fifth flow path 36 can flow a fluid for correction which does not contain particles and is different from the fluid containing the specific particles separated and recovered in the first flow path device 2. As a result, it is possible to measure the second flow path 16 and the fifth flow path 36 in sequence every time the specific particles are measured to estimate the number of specific particles in accordance with a difference of light intensity of the flow paths 16 and 36, thus an influence of deterioration of an optical sensor can be reduced.

The fifth flow path 36 includes a plurality of fifth openings 37 located in the pair of second upper and lower surfaces 17. The fifth openings 37 include a fifth flow inlet 38 and a fifth flow outlet 39. The fifth flow inlet 38 is an opening through which a fluid for correction flows into the fifth flow path 36. The fifth flow outlet 39 is an opening through which the fluid for correction flows from the fifth flow path 36.

The fifth flow inlet 38 of the plurality of fifth openings 37 is located in the same surface as that of the third opening 30. As a result, an operation of introducing and exhausting the fluid can be performed on the same surface from above. The fifth flow outlet 39 may be located in the second lower surface 20.

The second flow path device 3 may further include a sixth flow path 40 different from the second flow path 16, the third flow path 29, the fourth flow path 32, and the fifth flow path 36. The sixth flow path 40 includes a plurality of sixth openings 41 located in at least one of the pair of second upper and lower surfaces 17. The plurality of sixth openings 41 include a sixth flow inlet 42 and a sixth flow outlet 43. The sixth flow inlet 42 is an opening through which a fluid for a pressing flow flows into the sixth flow path 40. The sixth flow outlet 43 is an opening through which the fluid for a pressing flow flows from the sixth flow path 40. The sixth flow inlet 42 is located so that the fluid can be flowed therethrough, and the sixth flow outlet 43 is connected to the pressing flow inlet 15 of the first flow path device 2.

The third flow path 29, the fourth flow path 32, and the fifth flow path 36 can be formed in the manner similar to the second flow path 16.

(Connection Structure of First Flow Path Device 2 and Second Flow Path Device 3)

The first flow path device 2 is located on the second upper surface 19 of the second flow path device 3. Herein, a sheet member 44 may intervene between the first lower surface 11 of the first flow path device 2 and the second upper surface 19 of the second flow path device 3. In other words, the measurement flow path device 1 may include the sheet member 44 located between the first flow path device 2 and the second flow path device 3.

The sheet member 44 has a function as an intermediate layer for bonding hardly-adhesive materials. The sheet member 44 may be formed of a material such as silicone or PDMS, for example. The measurement flow path device 1 includes the sheet member 44, thereby being able to absorb a roll of a surface of a bonding surface. The sheet member 44 includes a plurality of through holes 45. The plurality of through holes 45 face the plurality of first openings 9. As a result, the fluid flows between the first flow path device 2 and the second flow path device 3 via the through holes 45.

The first flow path device 2 and the second flow path device 3 in the present disclosure are connected via an adhesive agent applied to a lower surface of the sheet member 44. It is sufficient that the adhesive agent is a photo-curable resin hardened by ultraviolet or a thermoplastic resin, for example.

(Particle Separation Apparatus)

Next, a particle separation apparatus according to the present disclosure is described. The particle separation device according to the present disclosure includes the first flow path device 2 which is the particle separation device, a first pump for flowing the sample into the sample flow inlet 12, and a second pump for flowing the fluid into the pressing flow inlet 15. The particle separation device is the first flow path device 2 described above, and the first pump is connected to the sample flow inlet 12 of the first flow path device 2 by a first tube, for example. The sample sent from the first pump flows into the sample flow inlet 12 of the first flow path device 2 through the first tube. The second pump is connected to the pressing flow inlet 15 of the first flow path device 2 by a second tube, for example. The fluid sent from the second pump flows into the pressing flow inlet 15 of the first flow path device 2 through the second tube. Accordingly, the specific particles, for example, the first particles P1 can be separated and recovered from the sample by the main flow path 5 and the plurality of branch flow paths 6 as described above.

Various known pumps can be used as the first pump and the second pump as long as they can send out the fluid. The first pump preferably has a function of flowing a small amount of fluid containing particles such as blood, for example, into the sample flow inlet 12 of the first flow path device 2 at a constant flow rate. The second pump preferably has a function of flowing a fluid for generating a pressing flow such as phosphate buffered saline (PBS), for example, into the pressing flow inlet 15 of the first flow path device 2 at an appropriate flow volume, flow rate, and pressure. A syringe pump, for example, can be preferably applied to the first pump and the second pump. The other pump such as an electroosmotic flow pump, a peristaltic pump, and a gas pump are also applicable.

The first tube and the second tube can be made up using a tube made of known various materials in accordance with a fluid to be used. When the sample is blood and the fluid is PBS, a silicon tube, for example, can be preferably applied. These tubes are not necessary, thus the particle separation apparatus needs not include these tubes when the first flow path device 2 is directly connected to the first pump and the second pump or connected via an adapter, for example.

(Measurement Apparatus)

Next, a measurement apparatus including the particle separation device according to the present disclosure is described.

Figure 8:
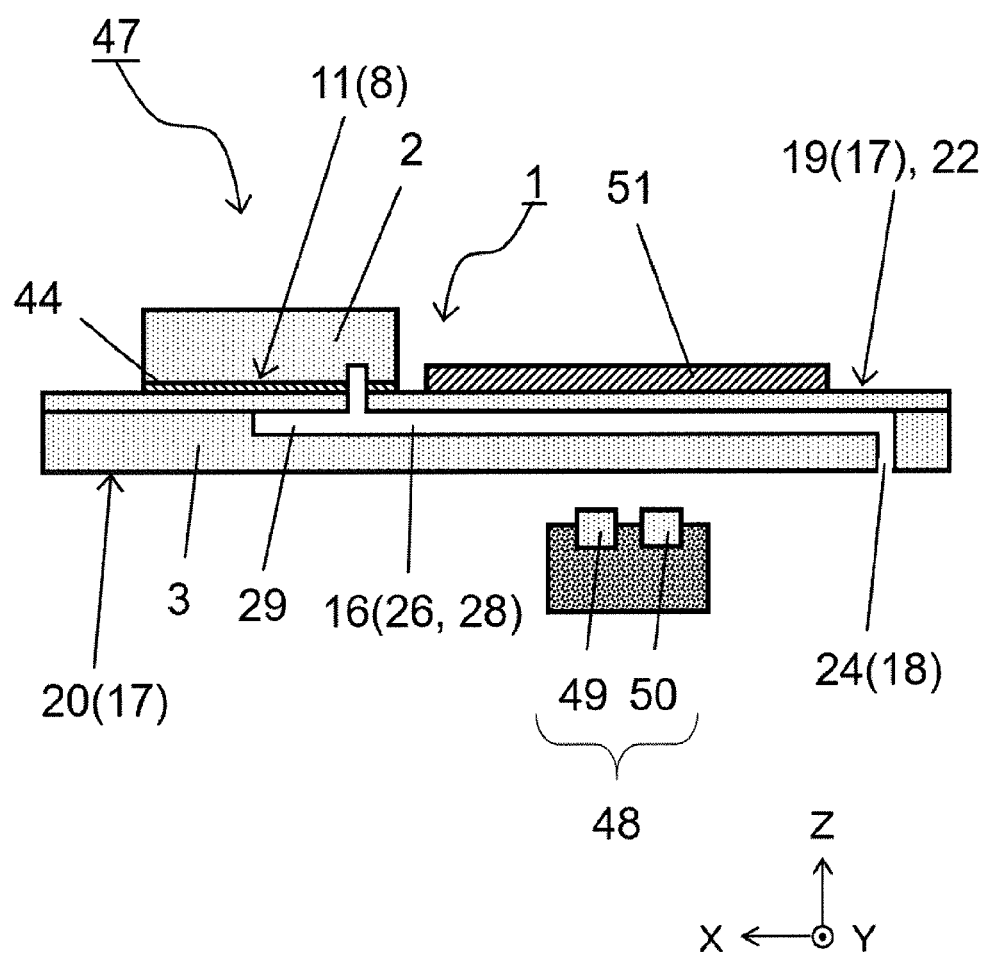
FIG. 8 illustrates a cross-sectional view showing an example of a measurement apparatus including the particle separation device according to the present disclosure.
Figure 9:
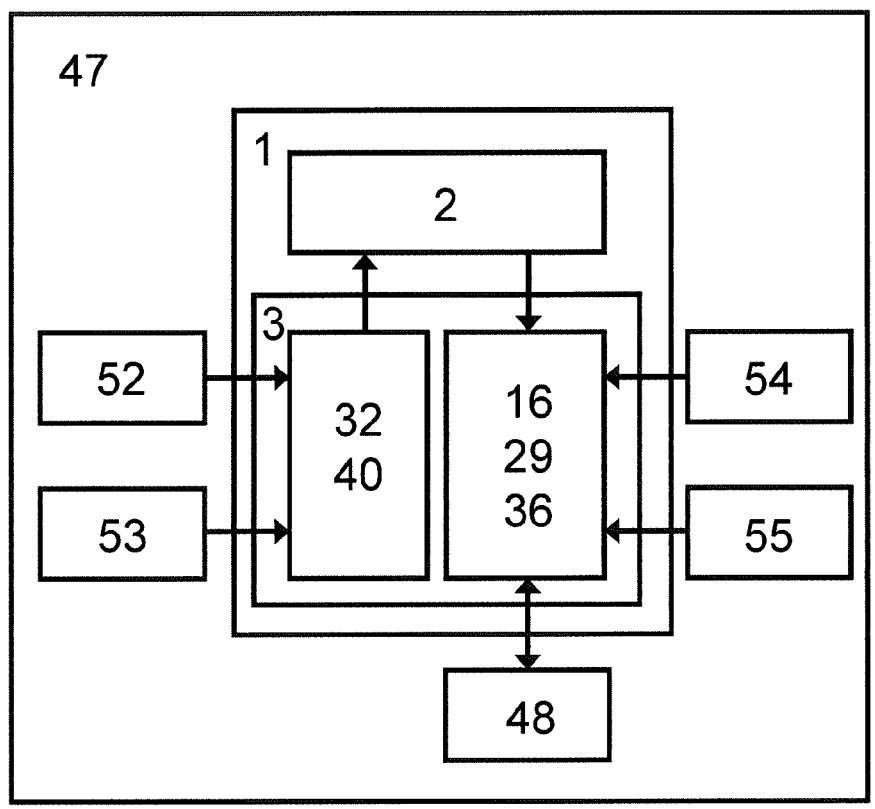
FIG. 9 illustrates a block diagram schematically showing an example of a whole configuration of the measurement apparatus including the particle separation device according to the present disclosure.

FIG. 8 and FIG. 9 schematically illustrate a measurement apparatus 47. FIG. 8 is a cross-sectional view of the measurement apparatus 47 with the same viewpoint as that in FIG. 2. Description of some of reference signs similar to those in FIG. 2 are omitted. FIG. 9 schematically illustrates a block diagram of an example of a whole configuration of the measurement apparatus 47.

The measurement apparatus 47 includes the measurement flow path device 1 and an optical sensor 48. The optical sensor 48 includes a light-emitting element 49 and a light receiving element 50. Accordingly, the measurement flow path device 1 can separate the required particles (for example, the first particles P1) from the sample. Then, the particles flowing to the second flow path 16 (the second planar part 28) of the measurement flow path device 1 is irradiated with light from the light-emitting element 49 of the optical sensor 48, and the light receiving element 50 of the optical sensor 48 receives the light passing through the second flow path 16 (the second planar part 28), thus the particles can be measured. Specifically, the light passing through the second flow path 16 is diffused, reflected, or absorbed by the particles (the first particles P1) in the sample, thus the light intensity decreases. A standard curve indicating a relationship between the sample including the particles, the number of which is already known, and an attenuation amount of the light is previously prepared and the attenuation amount of the light measured by the measurement apparatus 47 is checked against the standard curve, thus the particles in the sample can be measured.

The light-emitting element 49 may be a light emitting diode (LED), for example. The light receiving element 50 may be a photo diode (PD), for example. The light receiving element 50 includes a semiconductor substrate including a region of one conductivity type and a region of the other conductivity type to form a PD of the light receiving element 50 on an upper surface, and includes the light-emitting element 49 made up of a plurality of semiconductor layers stacked on the semiconductor substrate, for example.

A mirror member 51 is located on the second upper surface 19 of the second flow path device 3 in the measurement flow path device 1 of the measurement apparatus 47 according to the present disclosure. The light-emitting element 49 and the light receiving element 50 of the optical sensor 48 are located on the second lower surface 20 side of the second flow path device 3. Accordingly, the light receiving element 50 of the optical sensor 48 can receive the light emitting from the light-emitting element 49, passing through the second flow path 16 (the second planar part 28), and reflected from the mirror member 51. The mirror member 51 may be formed of a material such as aluminum or gold, for example. The mirror member 51 can be formed by an evaporation method or a sputtering method, and can also be formed by placing metal foil or the like, for example.

The measurement apparatus 47 further includes a first supply unit 52 supplying the sample, a second supply unit 53 supplying the fluid for the pressing flow, a third supply unit 54 supplying the extrusion fluid, and a fourth supply unit 55 supplying the correction fluid, all of which are connected to the measurement flow path device 1. The first supply unit 52 is connected to the fourth flow inlet 34. The second supply unit 53 is connected to the sixth flow inlet 42. The third supply unit 54 is connected to the third opening 30. The fourth supply unit 55 is connected to the fifth flow inlet 38. The measurement apparatus 47 includes a controller (not shown), and the controller controls the first supply unit 52, the second supply unit 53, the third supply unit 54, the fourth supply unit 55, and the optical sensor 48.

The present disclosure is not limited to the embodiments described above, however, various alternation and modifications, for example, should be possible within the scope of the present disclosure.

Figure 10:
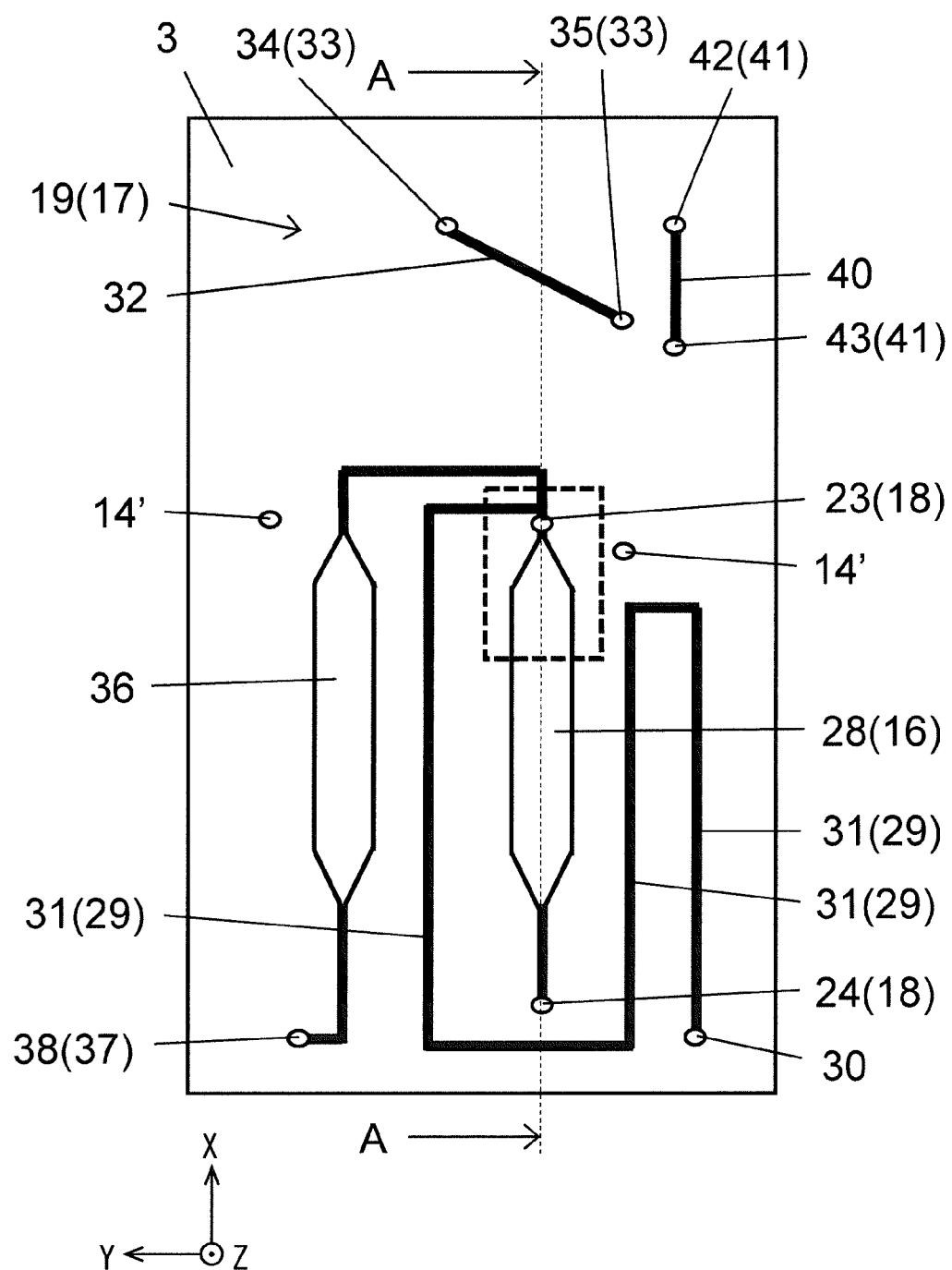
FIG. 10 illustrates a plan view showing the other example of the second flow path device used for the measurement flow path device including the particle separation device according to the present disclosure.
Figure 11:
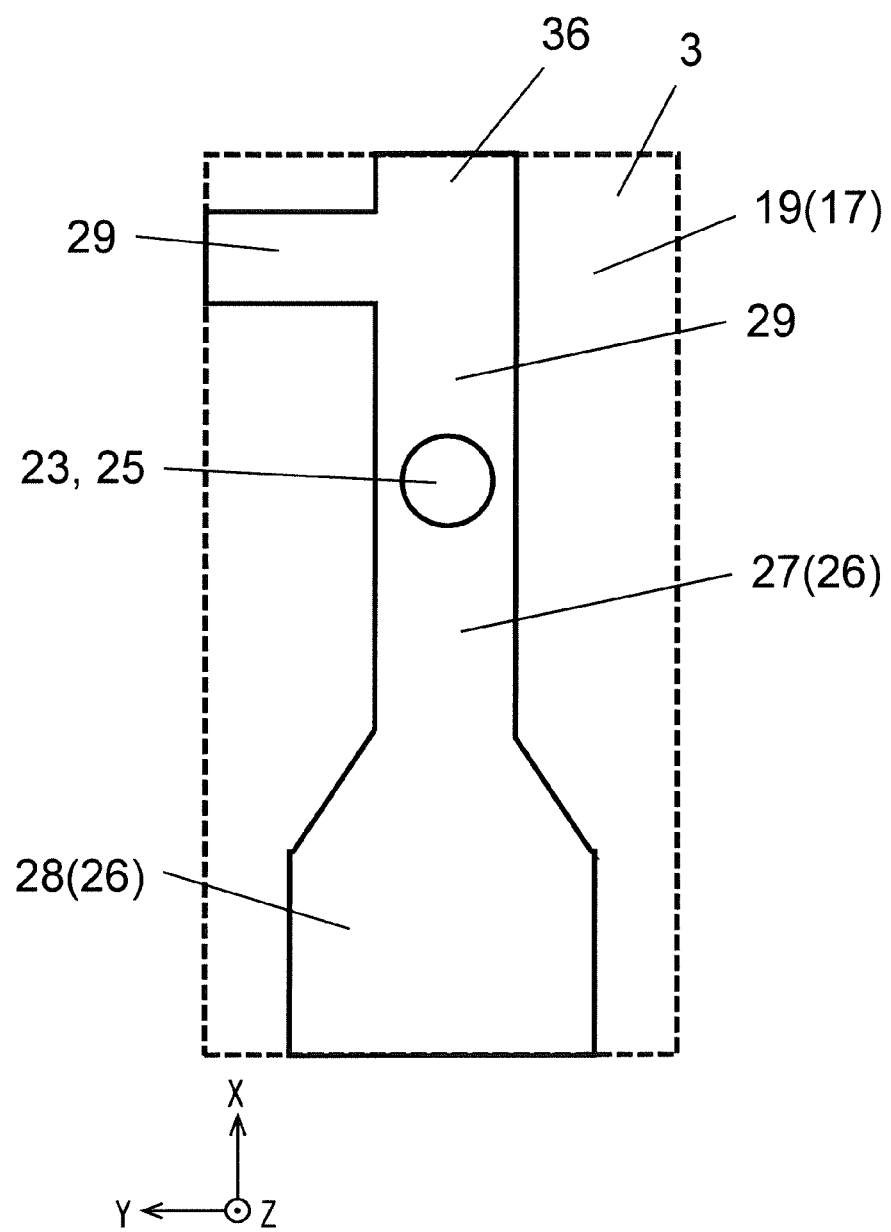
FIG. 11 illustrates a plan view showing a part of the other example of the second flow path device used for the measurement flow path device including the particle separation device according to the present disclosure.

The above embodiments describe the example that one end of the fifth flow path 36 includes the fifth flow outlet 39, however, as illustrated in FIG. 10 and FIG. 11, one end of the fifth flow path 36 may be connected to the second flow path 16. In this case, the fluid in the fifth flow path 36 can be injected into the second flow path 16, thus the above configuration has an effect that a concentration of the particles such as white blood cells in the second flow path 16 can be reduced. FIG. 10 and FIG. 11 are illustrated with the viewpoint similar to that in FIG. 6 and FIG. 7, and the detailed description is omitted.

The above embodiments describe the example that the measurement flow path device 1 includes the fifth flow path 36 and the sixth flow path 40, however, the fifth flow path 36 may function as the sixth flow path 40. That is to say, the fifth flow path 36 and the sixth flow path 40 may constitute one flow path to be connected to the first flow path 4 (the pressing flow inlet 15).

Figure 12:
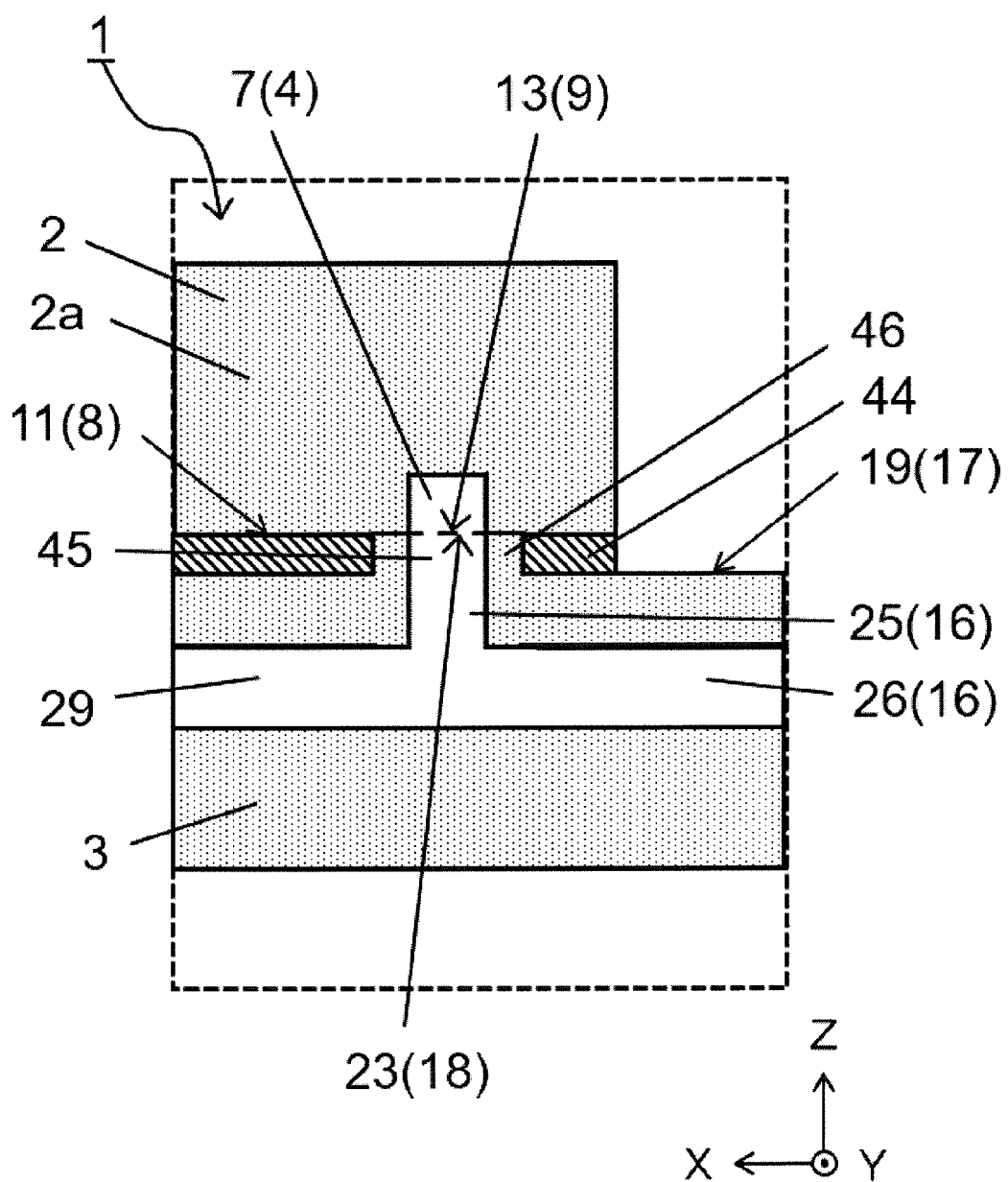
FIG. 12 illustrates a cross-sectional view showing a part of the other example of the measurement flow path device including the particle separation device according to the present disclosure.

The above embodiments describe the example that the first flow path device 2 and the second flow path device 3 are bonded via the sheet member 44, however, as illustrated in FIG. 12, the second flow path device 3 may further include a protruding portion 46 located around the opening on the second upper surface 19. The protruding portion 46 may be inserted into the plurality of through holes 45 of the sheet member 44. As a result, the first flow path device 2 and the second flow path device 3 can be connected to each other via the protruding portion 46. The adhesive agent needs not be provided between the first flow path device 2 and the protruding portion 46 if the connection of the first flow path device 2 and the second flow path device 3 can be secured only with the protruding portion 46. In the example illustrated in FIG. 12, the second flow path 16 and the second opening 18 are located in the protruding portion 46 and the first flow path 4 and the second flow path 16 are connected to each other via the protruding portion 46, however, it is also applicable that the protruding portion 46 is provided merely as a protruding-shaped part on the second upper surface 19 and used for positioning and bonding of the first flow path device 2 and the second flow path device 3. FIG. 12 is a cross-sectional view with the same viewpoint as that in FIG. 5, and the detailed description is omitted.

The first flow path device 2 and second flow path device 3 may be directly connected to each other without using an adhesive agent or the like. For example, they can be directly connected by applying a silane coupling agent to at least one of the first lower surface 11 of the first flow path device 2 or the second upper surface 19 of the second flow path device 3.

The above embodiments describe the example that the first flow path 4 is formed inside the base body 2a made up of the two substrates bonded to each other, however, the sheet member 44 may be used as one of the two substrates. That is to say, the first flow path 4 may be formed of one substrate and the sheet member 44.

Figure 13:
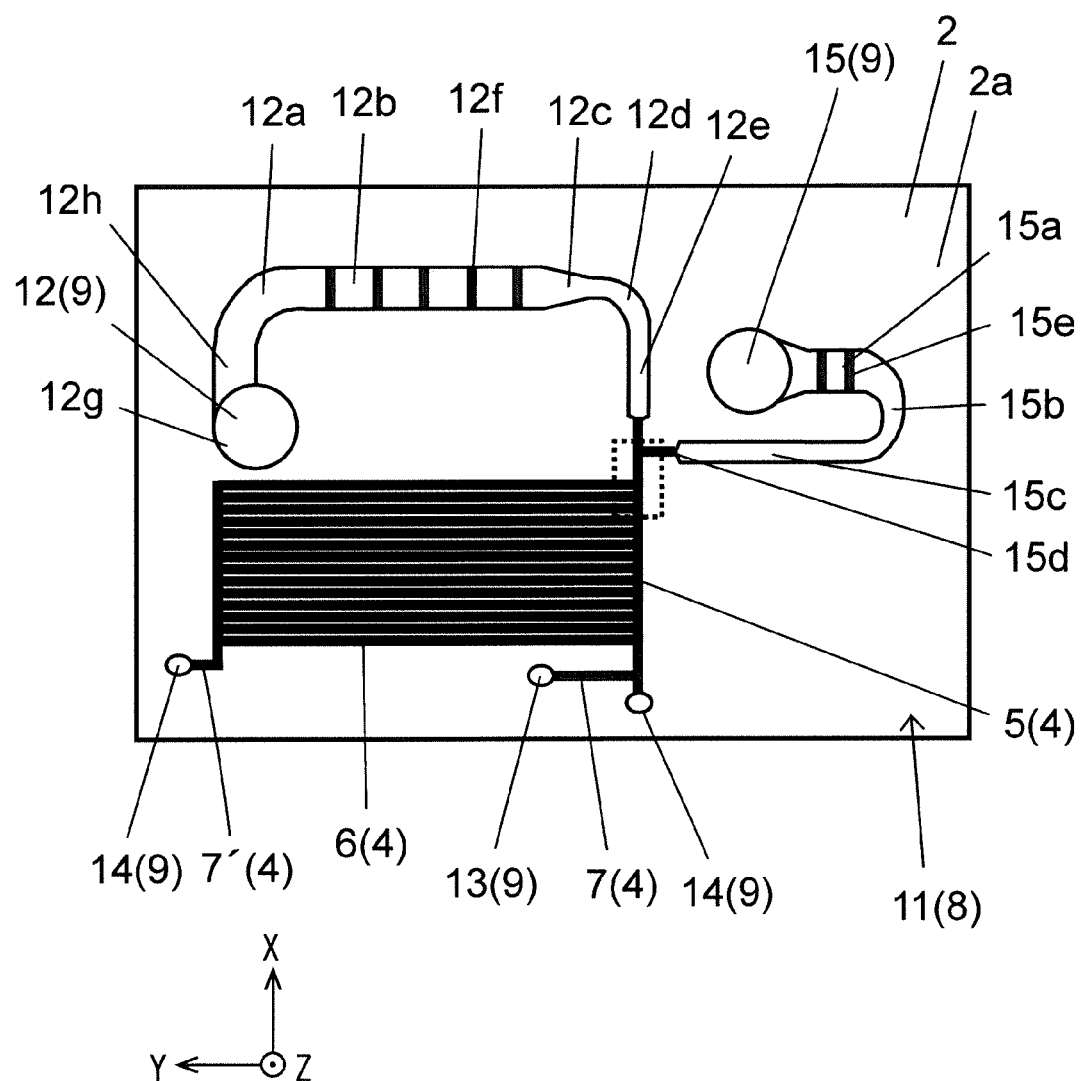
FIG. 13 illustrates a plan view showing the other example of the particle separation device according to the present disclosure.
Figure 14:
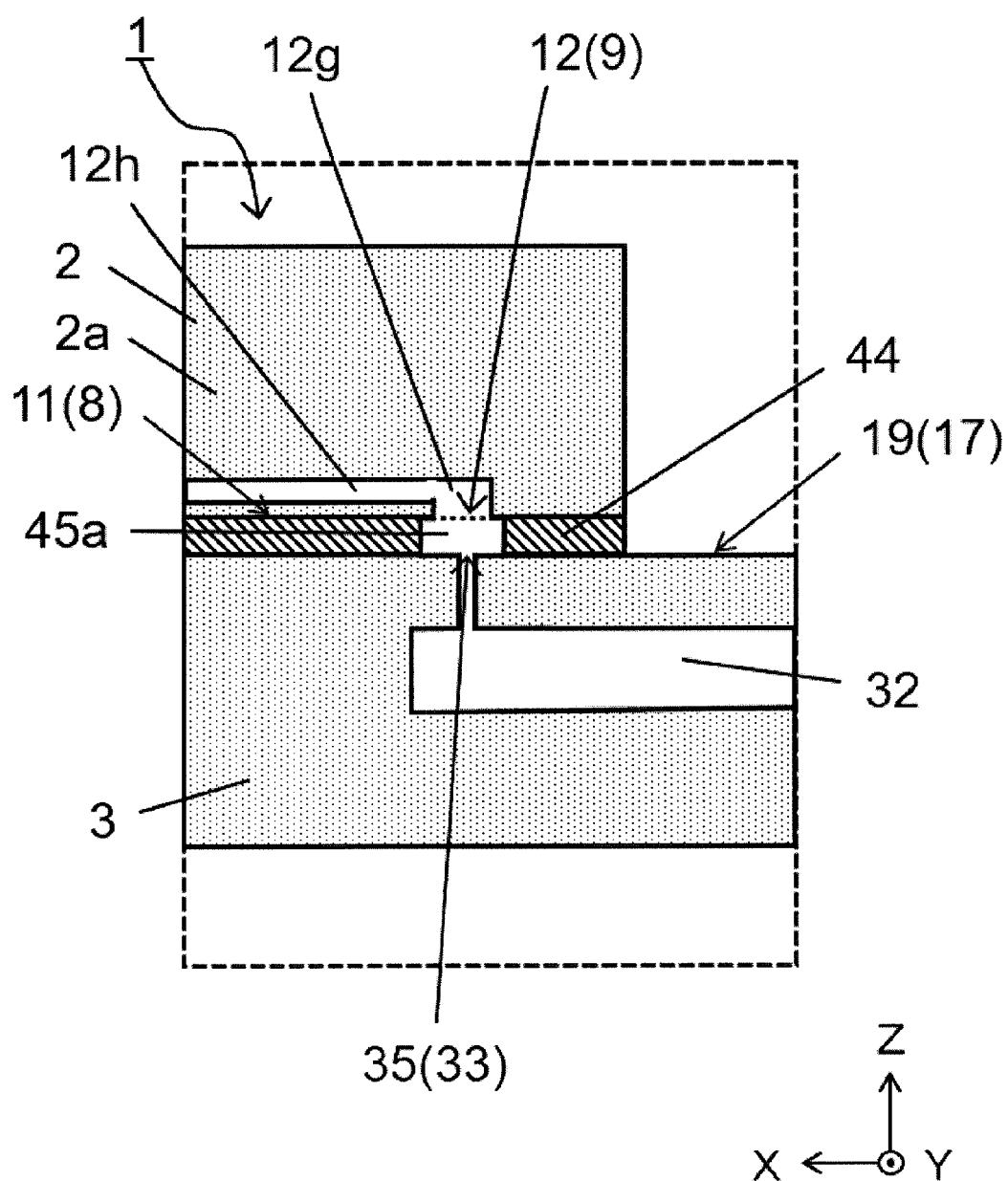
FIG. 14 illustrates a cross-sectional view showing a part of the other example of the measurement flow path device including the particle separation device according to the present disclosure.

The above embodiments describe the example that in the first flow path device 2, the sample flow inlet 12 is connected to the main flow path 5 via the first bending part 12a, the first straight part 12b, the second bending part 12d, and the second straight part 12e. In contrast, as illustrated in FIG. 13 and FIG. 14, it is preferable that the sample flow inlet 12 includes a pillar opening part 12g having a circular opening and a flow straight part 12h which is a straight flow path connected to the pillar opening part 12g and reaching the first bending part 12a, and the flow straight part 12h has a width smaller than the pillar opening part 12g and is located so that one side in a width direction follows a tangent line of the circular opening of the pillar opening part 12g. According to such a configuration, the fluid (sample) supplied to the pillar opening part 12g does not remain in the pillar opening part 12g but can pass therethrough smoothly, thus can be efficiently flowed toward the first bending part 12a through the flow straight part 12h. FIG. 13 and FIG. 14 are illustrated with the viewpoint similar to that in FIG. 3 and FIG. 5, and the detailed description is omitted.

A size of the pillar opening part 12g constituting the sample flow inlet 12 may have the same diameter as the first opening 9 described above, that is 1 to 3 mm, for example. A depth of the pillar opening part 12g may be a depth from the opening in the upper surface of the base body 2a to a bottom surface of the first bending unit 12a, for example, as with the first bending part 12a. A width of the flow straight part 12h may be 0.5 to 2.5 mm, for example, since the sample is flowed smoothly if the width thereof is the same as that of the first bending part 12a.

When the flow straight part 12h is located so that one side in the width direction follows the tangent line of the circular opening of the pillar opening part 12g, it is preferable that the flow of the sample follows a bending direction of the first bending part 12a so that a turbulent flow of the sample hardly occurs at the time of flowing in the first bending part 12a as illustrated in FIG. 13.

When such a first flow path device 2 is connected to the second flow path device 3, it is preferable that the first flow path device 2 further includes the sheet member 44 disposed around the pillar opening part 12g of the base body 2a and having a relay port 45a which is a through hole corresponding to the circular opening of the pillar opening part 12g, and a size of the relay port 45a is larger than the circular opening of the pillar opening part 12g as illustrated in FIG. 14. Accordingly, a pressure fluctuation from outside at the time of flowing the sample can be reduced, for example.

The fourth flow outlet 35 of the fourth flow path 32 in the second flow path device 3 is connected to the pillar opening part 12g and the relay port 45a, and a size of an opening of the fourth flow outlet 35 is preferably equal to or smaller than the size of the relay port 45a. It is preferable that the opening of the fourth flow outlet 35 is eccentrically located with respect to a concentric circle of the opening of the circular relay port 45a, that is to say, the opening of the fourth flow outlet 35 is located in a position deviated from the flow direction as much as possible in the sample flow inlet 12 (the pillar opening part 12g). Accordingly, the sample flowing into the pillar opening part 12g from the fourth flow outlet 35 via the relay port 45a flows along a circumference of the sample flow inlet 12 easily, thus the particles flows smoothly and an occurrence of an area where the particles remain in a region on a side opposite to the flow direction in the sample flow inlet 12 can be suppressed.

The invention claimed is:

1. A particle separation device comprising:
   a straight main flow path inside a plate-like base body, the straight main flow path including a flow outlet opened in at least one of an upper surface and a lower surface of the base body;
   a plurality of branch flow paths connected to a portion midway through a side surface of the straight main flow path in a direction perpendicular to the side surface, and a flow inlet opened in at least one of the upper surface and the lower surface of the base body,
   the flow inlet comprising
   a sample flow inlet through which a sample which is a fluid containing particles to be separated flows toward the straight main flow path; and
   a pressing flow inlet connected to a side surface of the straight main flow path located on an upstream side and opposite to the plurality of branch flow paths in a direction perpendicular to the side surface of the main flow path, said pressing flow inlet configured to press the sample flowing in the straight main flow path against a side of the at least one of the branch flow paths, wherein in a planar view of the base body, the sample flow inlet is connected to the main flow path via an R-shaped first bending part, a first straight part, an R-shaped second bending part, and a second straight part, and a width in the first bending part and a width in the first straight part are larger than a width in the second bending part and a width in the second straight part, and the width in the second bending part and the width of the second straight part are larger than a width in the straight main flow path; and the pressing flow inlet is connected to the side surface of the straight main flow path via a third straight part, an R-shaped third bending part, a fourth straight part, and a fifth straight part, and a width in the third straight part is larger than a width in the fourth straight part, and the width in the fourth straight part is larger than a width in the fifth straight part.

2. The particle separation device according to claim 1, wherein
   the first straight part and the second bending part are connected by a tapered part in which a width is gradually narrowed.

3. The particle separation device according to claim 1, wherein
   the third bending part has a width that is gradually narrowed from the third straight part to the fourth straight part.

4. The particle separation device according to claim 1, wherein
   provided in at least one of the first straight part and the third straight part is a pillar part made up of a plurality of pillar bodies, which are disposed in a width direction, each extending from a bottom surface to a ceiling surface.

5. The particle separation device according to claim 1, wherein
   a length of the second straight part is at least three times larger than the width of the second straight part, and a length of the fourth straight part is at least three times larger than the width of the fourth straight part.

6. The particle separation device according to claim 1, wherein
   the sample flow inlet includes
   a pillar opening part having a circular opening, and
   a flow straight part which is a straight flow path connected to the pillar opening part and reaching the first bending part,
   the flow straight part having a width smaller than the pillar opening part and located so that one side in a width direction follows a tangent line of the circular opening.

7. The particle separation device according to claim 6, further comprising
   a sheet member disposed around the pillar opening part of the base body and having a relay port which is a through hole corresponding to the circular opening, wherein
   a size of the relay port is larger than the circular opening.

8. A particle separation apparatus comprising:
   the particle separation device according to claim 1; and a first pump for flowing the sample into the sample flow inlet; and a second pump for flowing a fluid into the pressing flow inlet.

\* \* \* \* \*